(12) United States Patent
Baker et al.

(10) Patent No.: US 8,507,654 B2
(45) Date of Patent: Aug. 13, 2013

(54) ALTERED ANTIBODIES

(75) Inventors: Terence Seward Baker, Slough (GB); David Paul Humphreys, Slough (GB); Alastair David Griffiths Lawson, Slough (GB)

(73) Assignee: UCB Pharma S.A. (BE)

( * ) Notice: Subject to any disclaimer, the term of this patent is extended or adjusted under 35 U.S.C. 154(b) by 731 days.

(21) Appl. No.: 12/443,599

(22) PCT Filed: Sep. 28, 2007

(86) PCT No.: PCT/GB2007/003706
§ 371 (c)(1),
(2), (4) Date: Nov. 30, 2009

(87) PCT Pub. No.: WO2008/038024
PCT Pub. Date: Apr. 3, 2008

(65) Prior Publication Data
US 2010/0093977 A1   Apr. 15, 2010

(30) Foreign Application Priority Data
Sep. 29, 2006   (GB) .................................. 0619291.8

(51) Int. Cl.
*C07K 16/18*   (2006.01)
*A61K 49/00*   (2006.01)

(52) U.S. Cl.
CPC ................................ *A61K 49/0058* (2013.01)
USPC .................................................... 530/387.3

(58) Field of Classification Search
CPC .............................................. A61K 47/48215
USPC .................................................... 530/387.3
See application file for complete search history.

(56) References Cited

U.S. PATENT DOCUMENTS

2007/0092940 A1 *   4/2007   Eigenbrot et al. ........... 435/69.1

FOREIGN PATENT DOCUMENTS
WO   WO 2004/003019   *   6/2004

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Salfeld (Nature Biotech. 25(12): 1369-1372 (2007)).*
Dall'Acqua (J. Immunol. 177:1129-1138 (2006)).*
Ibragimova and Eade (Biophysical Journal, Oct 1999, vol. 77, pp. 2191-2198).*
Burgess et al, Journal of Cell Biology vol. 111 Nov. 1990 2129-2138.*
Schwartz et al, Proc Natl Acad Sci USA vol. 84:6408-6411 (1987)).*
Lin et al Biochemistry USA vol. 14:1559-1563 (1975)).*
Lazar et al Molecular and Cellular Biology Mar. 1988 vol. 8 No. 3 1247-1252).*
Harris et al (Nature 2:214-221 (Mar. 2003)).*
Renard, M., Improving the Sensitivity and Dynamic Range of Reagentless Fluorescent Immunosensors by Knowledge-Based Design, Biochemistry, 2004, pp. 15453-15462, vol. 43.
Shopes, B., A Genetically Engineered Human IGG with Limited Flexibility Fully Initiates Cytolysis Via Complement, Molecular Immunology, pp. 603-609, Elmsford, NY.
Butlin, N. et al., Antibodies with Infinite Origins and Applications, 2006, Acc. Chem. Res., pp. 780-787, vol. 39.
Renard, M. et al., Deriving Topological Constraints from Functional Data for the Design of Reagentless Fluorescent Immunosensors, Journal of Molecular Biology, Feb. 7, 2003, pp. 167-175, London.
International Search Report dated Feb. 7, 2008.
Heywood, S. and Humphreys, D., "Polymer Fusions to Increase Antibody Half-Lives: PEGylation and Other Modifications", Chapter 19, Recombinant Antibodies for Immunotherapy, Cambridge University Press, 2009.

* cited by examiner

*Primary Examiner* — Lynn Bristol
(74) *Attorney, Agent, or Firm* — McDonnell Boehnen Hulbert & Berghoff

(57) ABSTRACT

This invention relates to engineering of antibodies and more specifically provides altered antibodies of the IgG class to which one or more effector molecules are attached. The invention further relates to methods for the production of such conjugated antibodies.

9 Claims, 3 Drawing Sheets

(a)

QIQLVQSGAEVKKPGSSVKVSCKASGYTFTDYYINWMRQAPGQGLEWIGWIDPGSGN
TKYNEKFKGRATLTVDTSTNTAYMELSSLRSEDTAFYFCAREKTTYYYAMDYWGQGT
LVTVSSASTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKYGPPCPS
CPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK (b)

DIQMTQSPSTLSASVGDRVTITCRSSKSLLHSNGDTFLYWFQQKPGKAPKLLMYRMS
NLASGVPSRFSGSGSGTEFTLTISSLQPDDFATYYCMQHLEYPFTFGQGTKVEVKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC (c)

DIQMTQSPSTLSASVGDRVTITCRSSKSLLHSNGDTFLYWFQQKPGKAPKLLMYRMS
NLASGVPSRFSGSGSGTEFTLTISSLQPDDFATYYCMQHLEYPFTFGQGTKVEVKRT
VAAPSVFIFPPSDEQLKSGTASVVCLLNNFYPREAKVQWKVDNALQSGNSQESVTEQ
DSKDCTYSLSSTLTLSKADYEKHKVYACEVTHQGLSSPVTKSFNRGEC

RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

(b)

RTVAAPSVFIFPPSDEQLKSGTASVVCLLNNFYPREAKVQWKVDNALQ<u>C</u>GNSQESVT
EQDSKDSTYSLSSTLTLSKADYEKHKVYACEVTHQGLSSPVTKSFNRGEC

(c)

RTVAAPSVFIFPPSDEQLKSGTASVVCLLNNFYPREAKVQWKVDNALQSGNSQESVT
EQDSKDSTYSLSSTLTLSKADYEKHKVYACEVTHQGL<u>C</u>SPVTKSFNRGEC

(d)

RTVAAPSVFIFPPSDEQLKSGTASVVCLLNNFYPREAKVQWKVDNALQSGNSQESVT
EQDSKDSTYSLSSTLTLSKADYEKHKVYACEVTHQGLS<u>C</u>PVTKSFNRGEC

Figure 2

ALTERED ANTIBODIES

This is a National Stage of International Application No. PCT/GB2007/003706, filed Sep. 28, 2007.

The present invention relates to engineering of antibodies and more specifically provides altered antibodies of the IgG class to which one or more effector molecules are attached. Further provided are methods for their production.

Antibodies are generally Y-shaped molecules comprising two identical heavy chains and two identical light chains. Disulfide bonds link together the heavy and light chain pairs, the N-terminal portion of which comprise the antigen binding sites. Disulfide bonds also link together the two heavy chains, the C-terminal portion of which (the Fc portion) lacks the ability to bind antigen. This Fc portion is involved in mediating activities such as complement fixation, transplacental passage and binding to various cell types. Effector functions associated with Fc binding include, for example, phagocytosis, antibody-dependent cell cytotoxicity (ADCC), complement-dependent cytotoxicity (CDC) and endocytosis. These functions can be of importance in mediating the therapeutic effect of an antibody. Antibody-drug conjugates with the potential for effector function are typically of the class IgG1.

The high specificity and affinity of antibodies make them ideal diagnostic and therapeutic agents, particularly for modulating protein:protein interactions. Both whole antibodies and engineered antibody fragments are proving to be versatile therapeutic agents, as seen by the recent success of products such as ReoPro (chimeric antibody Fab fragment), Rituxan (chimeric IgG1), Remicade™ (chimeric IgG1), Herceptin (humanized IgG1), and Humira (human IgG1). Specifically of interest are humanized antibodies and fragments thereof that are aimed at reducing or eliminating the inherent immunogenicity associated with non-human monoclonal antibodies.

Of particular therapeutic interest are antibody-conjugates wherein an effector molecule such as a drug, toxin, or label is linked to the antibody. Effector molecules may be attached to antibody fragments by a number of different methods, including through aldehyde sugars or more commonly through any available amino acid side-chain or terminal amino acid functional group located in the antibody fragment, for example any free amino, imino, thiol, hydroxyl or carboxyl group. The site of attachment of effector molecules can be either random or site-specific. Random attachment is often achieved through amino acids such as lysine and this results in effector molecules being attached at a number of sites throughout the antibody fragment depending on the position of the lysines. While this has been successful in some cases the exact location and number of effector molecules attached cannot be controlled and this can lead to loss of activity, for example if too few are attached, or can lead to loss of affinity, for example if the attachment interferes with the antigen binding site (Chapman 2002 Advanced Drug Delivery Reviews, 54, 531-545). As such, the coupling is random resulting in a non-homogeneous, ill-defined antibody-conjugate product.

In contrast, controlled site-specific attachment of effector molecules, such as attachment via existing cysteine residues, offers considerable advantages over random-site attachment. Nevertheless, site specific attachment has unpredictable results in that there can be loss of Fc effector function and/or loss of antigen-binding ability through disruption of tertiary structure. Antibodies with one or more engineered cysteine residues also suffer from the latter problems; for example, the engineered cysteine residue(s) may form a disulphide bond with an existing free thiol present within the antibody. The present invention, however, provides antibodies with at least one site-specific mutated residue permitting the production of a homogeneous well-defined product that retains antigen-binding ability and, where the antibody is a whole antibody, a homogeneous well-defined product that also retains potential Fc region effector function.

WO2006034488 discloses several antibodies in which specific heavy and light chain residues have been mutated to a cysteine residue. However, WO2006034488 does not specifically disclose mutation of the kappa light chain residues 171, 156, 202 or 203 of a human IgG to a cysteine residue.

Thus, the present invention provides the first disclosure of mutagenesis of any one or more of residues 171, 156, 202 and 203 (numbered according to the Kabat numbering system set forth in Kabat et al., 1987, in Sequences of Proteins of Immunological Interest, US Department of Health and Human Services, NIH, USA) of the kappa light chain to a cysteine residue, enabling site specific attachment of an effector molecule to the mutated residue. Further, the invention provides an antibody altered at the equivalent position, numbered according to the Kabat numbering system, in the lambda light chain.

Accordingly, provided is an altered antibody of the class IgG comprising at least one human kappa light chain, or an epitope-binding fragment thereof comprising said alteration, wherein the alteration comprises replacing at least one residue selected from the group consisting of residues 171, 156, 202 and 203, numbered according to the Kabat numbering system, of the at least one kappa light chain with a cysteine residue. In one embodiment, the residue altered is residue 156. In another embodiment, the residue altered is residue 171. In yet another embodiment, the residue altered is residue 202, and in a further embodiment, the residue altered is residue 203. Most preferably, the residue altered is residue 171.

The IgG class of an antibody of the invention may be human subclass IgG1, IgG2, IgG3 or IgG4. In particular, the IgG1 and IgG3 isotypes may be used when the antibody molecule is intended for therapeutic uses and antibody effector functions are desired, for example, antibody dependent cell-mediated cytotoxicity (ADCC) and/or complement dependent cytotoxicity (CDC). Most preferably, where the antibody comprises an Fc region, the antibody belongs to the IgG1 subclass. Alternatively, IgG2 and IgG4 isotypes may be used when the antibody molecule is intended for therapeutic purposes where antibody effector functions are not required.

Thus, antibodies of the present invention include antibodies which can possess effector function and, thus, may mediate ADCC and/or CDC. Accordingly, in one aspect, provided are altered antibodies of the invention which effect ADCC and/or CDC. In another aspect, the antibody has a functional effect, for example, the antibody is a blocking antibody, a neutralizing antibody, an agonistic or an antagonistic antibody. Most preferably, an antibody which mediates ADCC or CDC also has a further functional effect, for example, the antibody may be a blocking or neutralizing antibody preventing or interfering with the binding of antigen, e.g. a ligand. Alternatively, or additionally, the antibody may inhibit or activate a signalling pathway directly or indirectly. In another aspect of the invention, an antibody may be used to inhibit the activity of its cognate antigen. In a further aspect, the antibody is pro-apoptotic.

Antibodies generated against a desired antigen may be obtained by administering the antigen to a subject, preferably a non-human animal, using well-known and routine protocols. Thus, antibodies for use in the invention may be produced by any suitable method known in the art. Such antibodies include, but are not limited to, polyclonal, monoclonal, humanized, fully human, phage display-derived antibodies or chimeric antibodies. Also included are antibodies in which one or more complementarity-determining regions (CDRs) has been transferred from another species (a CDR-only transferred antibody). It will be appreciated that humanized antibodies includes those antibodies in which one or more residues within one or more CDRs has been humanized. These antibodies can be then subjected to alteration within the kappa light chain at one or more sites selected from the group consisting of residue 171, 156, 202 and 203. The term 'antibody' as used herein includes intact (whole) antibodies and functionally active fragments such as epitope binding fragments or derivatives thereof and may be, but are not limited to, single chain antibodies, bi, tri or tetra-valent antibodies, Bis-scFv, scFv-Fc, minibodies, diabodies, triabodies, tetrabodies, single domain antibodies, modified Fab fragments, Fab fragments, Fab' and F(ab')$_2$ fragments and epitope-binding fragments of any of the above (see, for example, Holliger and Hudson, 2005, Nature Biotech. 23(9): 1126-1136; Wu & Senter, 2005, Nature Biotech. 23(9):1137-1145).

Monoclonal antibodies may be prepared by any method known in the art such as the hybridoma technique (Kohler & Milstein, Nature, 1975, 256:495-497), the trioma technique, the human B-cell hybridoma technique (Kozbor et al., Immunology Today, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA, 93(15), 7843-7848, WO 92/02551, WO2004/051268, WO2004/106377, WO2005019824 and WO2005019823.

Chimeric antibodies are those antibodies encoded by immunoglobulin genes that have been genetically engineered so that the light and heavy chain genes are composed of immunoglobulin gene segments belonging to different species.

Humanized antibodies are antibody molecules having one or more complementarity determining regions (CDRs) from a non-human species and a framework region from a human immunoglobulin molecule (see, for example, U.S. Pat. No. 5,585,089).

The methods for creating and manufacturing recombinant antibodies are well known in the art (see for example, Boss et al., U.S. Pat. No. 4,816,397; Cabilly et al., U.S. Pat. No. 6,331,415; Simmons et al., 2002, Journal of Immunological Methods, 263, 133-147; Shrader et al., WO 92/02551; Orlandi et al., 1989, Proc. Natl. Acad. Sci. USA, 86, 3833; Riechmann et al., 1988, Nature, 322, 323; Queen et al., U.S. Pat. No. 5,585,089; Adair, WO91/09967; Mountain and Adair, 1992, Biotechnol. Genet. Eng. Rev, 10, 1-142; Verma et al., 1998, J. Immunol. Methods, 216:165-181; Holliger and Hudson, 2005, Nature Biotech. 23(9):1126-1136).

The antibodies for use in the present invention can also be generated using various phage display methods known in the art and include those disclosed by Brinkman et al., 1995, J. Immunol. Methods, 182:41-50; Ames et al., 1995, J. Immunol. Methods, 184, 177-186; Kettleborough et al. 1994, Eur. J. Immunol., 24, 952-958; Persic et al., 1997, Gene, 187, 9-18; and Burton et al., 1994, Advances in Immunol., 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Also, transgenic mice, or other organisms, including other mammals, may be used to produce antibodies (see for example U.S. Pat. No. 6,300,129).

The antibodies of the present invention will, in general, be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigens such as those antigens upregulated during disease or infection, for example receptors and/or their corresponding ligands. Particular examples of cell surface antigens include adhesion molecules, for example, integrins such as β1 integrins e.g. VLA-4, E-selectin, P-selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), BCMP7, CD137, CD27L, CDCP1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP11, DTD, MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumour necrosis factor-β, colony stimulating factors such as G-CSF or GM-CSF, and platelet derived growth factors such as PDGF-α, and PDGF-β and where appropriate receptors thereof.

The nucleic acid sequence of an antibody can be engineered by any method known in the art to produce the cysteine engineered kappa chain antibodies of the present invention, ie. S171C, S156C, S202C and S203C. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N.Y., 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, wild type and mutant versions of human kappa chains can be made by total gene synthesis by annealing, ligation and PCR amplification and cloning of overlapping oligonucleotides.

DNA encoding the antibody for engineering is obtainable using well-known methods, for example from a hybridoma cell or other antibody-producing cell.

The present invention also provides a method for the preparation of a cysteine engineered antibody of the invention. Accordingly, provided is a method for the preparation of an altered antibody of the class IgG comprising at least one human kappa light chain, or an epitope-binding fragment thereof comprising said alteration, comprising mutating at least one residue selected from the group consisting of residues 171, 156, 202 and 203, numbered according to the Kabat numbering system, with a cysteine residue. Most preferably, the method comprises mutating serine 171 of at least one kappa light chain of a human antibody of the class IgG.

In a particular aspect, cysteine engineered antibodies of the present invention can be conjugated to a therapeutic agent, such as a cytotoxic agent, a radionuclide or drug moiety to modify a given biological response, e.g. to inhibit cellular proliferation, to treat a disease, or to induce apoptosis. The therapeutic agent is not to be construed as limited to classical chemical therapeutic agents. Thus, an antibody for use in the present invention may be conjugated to one or more effector molecules. It will be appreciated that the effector molecule may comprise a single effector molecule or two or more such molecules so linked as to form a single moiety that can be attached to the antibodies of the present invention via the cysteine engineered at one or more of residue 171, 156, 202 or 203, numbered according to the Kabat numbering system. A further advantage offered by the conjugated antibodies of the present invention is that the regions giving rise to anti-idiotype may be masked by the effector molecule. In a preferred aspect, the invention provides an altered antibody comprising at least one human kappa light chain, or an epitope-binding fragment thereof comprising said alteration, wherein the alteration comprises the replacement of at least one residue selected from the group consisting of residues 171, 156, 202 and 203, numbered according to the Kabat numbering system, of the at least one kappa light chain with a cysteine residue, and wherein said altered antibody is conjugated to one or more effector molecules. In a preferred aspect, an altered antibody of the invention comprises at least one serine 171 to cysteine alteration with an effector molecule attached to said cysteine 171 residue. Most preferably, the invention comprises an antibody comprising two kappa light chains, each with serine 171 mutated to a cysteine residue and wherein each cysteine 171 has an effector molecule attached. Thus, the altered antibody may be a whole antibody, a Fab, Fab' or F(ab')$_2$ fragment, or a diFab or triFab altered at one or more residues selected from the group consisting of residue 171, 156, 202 and 203 to a cysteine residue, and wherein an effector molecule is conjugated via said cysteine residue (most preferably via residue 171). In one example, the antibody is a Fab' fragment with a S171C alteration wherein an effector molecule is conjugated directly or indirectly to the cysteine residue and a further effector molecule is conjugated to the heavy chain constant region C-terminal to the hinge region.

The term 'effector molecule' as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include auristatins, combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, anti-folates (e.g. aminopterin and methotrexate), antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines [e.g. daunorubicin (formerly daunomycin) and doxorubicin], antibiotics [e.g. dactinomycin (formerly actinomycin), bleomycin, mithramycin, anthramycin (AMC), calicheamicins or duocarmycins, CC-1065, enediyenes, neocarzinostatin), and anti-mitotic agents (e.g. vincristine and vinblastine]. See Garnett, 2001, Advanced drug Delivery Reviews 53:171-216 for further details.

Other effector molecules may include chelated radionuclides such as $^{131}$I, $^{111}$In and Y$^{90}$, Y$^{86}$, Lu$^{177}$, Bi$^{213}$, Cu$^{64}$, F$^{18}$, Ga$^{68}$, I$^{124}$, I$^{124}$, Tc$^{99m}$, Californium$^{252}$, Iridium$^{192}$ and Tungsten$^{188}$/Rhenium$^{188}$, $^{211}$astatine; or drugs such as but not limited to, alkylphosphocholines, topoisomerase I inhibitors, taxoids and suramin. Further effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a maytansinoid (for example, but not limited to, DM1), a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, angiogenin, gelonin, a dolstatin, minor groove binders, bis-iodo-phenol mustard (e.g. ZD2767P), or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor. In one preferred embodiment, the effector molecule is a minor groove binder.

Other effector molecules may include detectable substances useful, for example, in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See, generally, U.S. Pat. No. 4,741,900 for metal ions that can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and and suitable radioactive nuclides include $^{125}$I, $^{131}$I, $^{111}$In and $^{99}$Tc.

In a further example, the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, dextran, hydroxypropylmethacrylamide (HPMA), albumin, albumin-binding proteins or peptides or albumin-binding compounds such as those described in PCT/GB2005/002084 and in WO2006034488.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide. See for example (Veronese and Pasut, 2005, Drug Discovery Today, 10(21):1451-1458; Pasut et al., 2004, Expert Opinion in Therapeutic Patents, 14(6):859-894).

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumours or extend circulating half-life (for a review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15,000 Da to about 40,000 Da.

In one example antibodies for use in the present invention are attached to poly(ethyleneglycol) (PEG) moieties. In one particular example the antibody is an antibody fragment and the PEG molecules may be attached through a cysteine residue located at position 171, 156, 202 or 203, which cysteine residue may occur naturally in the antibody fragment or may be engineered into the fragment using recombinant DNA methods (see for example U.S. Pat. Nos. 5,219,996; 5,667,425; WO98/25971). Multiple sites can be used to attach two or more PEG molecules.

Thus, PEG molecules can be covalently linked through a thiol group of at least one cysteine residue located at residue 171, 156, 202 or 203, numbered according to the Kabat numbering system, in the human kappa light chain. Most preferably, a PEG molecule is linked directly or indirectly via the altered residue S171C. In a preferred embodiment, two PEG molecules are attached via each cysteine 171. Each polymer molecule attached to the modified antibody fragment may be covalently linked to the sulphur atom of a cysteine residue located in the fragment. The covalent linkage will generally be a disulphide bond or, in particular, a sulphur-carbon bond. Thus, thiol selective derivatives such as maleimides and cysteine derivatives may be used. An activated polymer may be used as the starting material in the preparation of polymer-modified antibody fragments as described above. The activated polymer may be any polymer containing a thiol reactive group such as, but without limitation, an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly (ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. Thus, in one preferred embodiment, an altered antibody of the invention is a Fab fragment comprising a human kappa light chain altered at residue 171, 156, 202 or 203 (most preferably at residue 171), numbered according to the Kabat system, to a cysteine residue, said antibody being pegylated with a linear PEG polymer of molecular weight about 20,000 Da or with a branched chain PEG polymer of molecular weight about 40,000 Da. In another preferred embodiment, an altered antibody of the invention is a Fab' fragment comprising a human kappa light chain altered at residue 171, 156, 202 or 203 (most preferably at residue 171), numbered according to the Kabat system, to a cysteine residue, said antibody being pegylated with a linear PEG polymer of molecular weight about 20,000 Da attached at said cysteine or with a branched chain PEG polymer of molecular weight about 40,000 Da and which is also pegylated by attachment of PEG to a cysteine in the hinge region. In another example, an altered Fab' fragment with a cysteine alteration in the human kappa light chain has a maleimide group covalently linked to the thiol of the altered amino acid residue (ie. cysteine 171, 156, 202 or 203, preferably cysteine 171) and a maleimide group linked to a free thiol in the hinge region. A lysine residue may be covalently linked to the maleimide group and to each of the amine groups on the lysine residue may be attached a methoxypoly(ethyleneglycol) polymer having a molecular weight of approximately 20,000 Da.

Cysteine 171, 156, 202 and 203 engineered antibodies of the invention have the advantage that such antibodies may have an effector molecule or molecules coupled site specifically to the one or two cysteine residues using a thiol-reactive reagent. In one aspect, such coupling is without loss of antigen recognition, and in another aspect is without loss of Fc region effector function. In a third aspect, where the effector molecule is a PEG molecule, such coupling may possibly reduce the propensity of the idiotypic region to elicit an immune response after administration to a subject.

It is well known that biosynthetically produced proteins containing free cysteine residues may in fact have the cysteine thiol blocked with adducts such as glutathione. Thus, before the thiol can be used as a point of coupling in a conjugation reaction, the adducts have to be removed by mild reduction. In the case of IgG, apart from the introduced cysteine, e.g. cysteine 171, 156, 202 and/or 203, on each of the kappa (or lambda) chains, there are a number of cysteine residues that form intra and inter-chain disulphide bonds and maintain the integrity of the IgG which may also be susceptable to reduction. The skilled person will therefore understand that it may be necessary to titrate the reducing agent in order to determine whether specific reduction of the kappa chain introduced cysteine residue(s) has been achieved without destablising the native disulphide bonds.

Thiol-reactive reagents include agents in which the reactive group is a maleimide, an iodoacetamide, a vinyl sulphone, a pyridyl disulphide or other thiol-reactive group (see Haugland 2003, Molecular Probes Handbook of Fluorescent Probes and research Chemicals; Brinkley, 1992, Bioconjugate Chem. 3:2; Garman, 1997, Non-radioactive labelling: A Practical Approach, Academic Press, London; Means, 1990, Bioconjugate Chem. 1:2; Hermanson, in Bioconjugate Techniques, 1996, Academic Press, San Diego, pp 40-55 & 643-671; Singh, 2002, Anal. Biochem. 304:147; Harlow & Lane, 1999, Using Antibodies: A Laboratory manual, Cold Spring Harbour Laboratory press, Cold Spring Harbour, N.Y.; Lundblad, 1991, Chemical Reagents for Protein Modification, $2^{nd}$ Ed, CRC Press, Boca Raton, Fla.).

Monothiol reducing agents for use in the present invention are widely known in the art examples of which include, but are not limited to, β-mercaptoethylamine, β-mercaptoethanol, cysteine and reduced glutathione. Preferably the monothiol reducing agent for use in the present invention is β-mercaptoethylamine.

Preferably, reduction is performed using 2-mercaptoethylamine at a concentration from 0.01 mM to 8 mM. The temperature range may be from 4° C. to 40° C. with room temperature to 37° C. being preferred and 37° C. being most preferred, for example for up to 24 hours.

Preferably, the concentration range is 0.1 to 5 mM, more preferably 0.5 mM to 4 mM, or 1 mM to 3 mM. Most preferably, the concentration range is from 1 mM to 2 mM and is intended to include the concentrations 1.1, 1.2, 1.3, 1.4, 1.5, 1.6, 1.7, 1.8 and 1.9 mM.

The skilled person will understand the equivalent concentrations of other reducing agents. Thus, for example, 2-mercaptoethanol may be used at from 0.01 to 3 mM and, more preferably, 0.5 to 2 mM.

Other suitable reducing agents include multi-thiol reducing agents which are incapable of forming intramolecular disulphide bonds. The term 'multi-thiol reducing agents which are incapable of forming intramolecular disulphide bonds' as used herein refers to reducing agents containing two or more thiol groups which are incapable of forming intramolecular disulphide bonds between the thiol groups. Examples of such reducing agents are shown below:

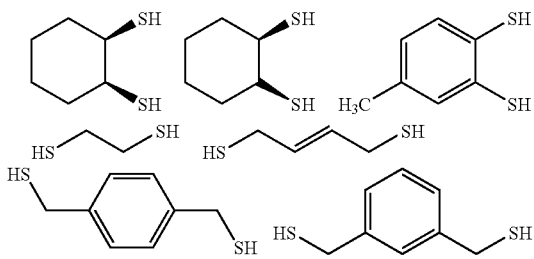

-continued

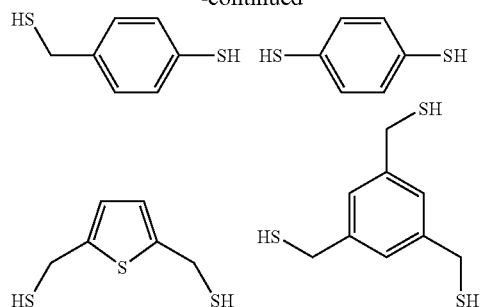

Unsuitable reducing agents for use in the present invention are multi-thiol reducing agents which are capable of forming intramolecular disulphide bonds, for example, dithiothreitol which can form an intramolecular disulphide bond between its two thiol groups.

It will be clear to a person skilled in the art that suitable reducing agents may be identified by determining the number of free thiols produced after the protein is treated with the reducing agent in step (a) or by determining the number of effector molecules attached in step (b) for example by size exclusion chromatography. Methods for determining the number of free thiols are well known in the art, see for example Lyons et al., 1990, Protein Engineering, 3, 703. Suitable concentrations of reducing agent may also be determined empirically by a person skilled in the art. Preferably the concentration of reducing agent is low in order to achieve selective activation of target cysteines.

Accordingly, provided is a method for the site-specific attachment of an effector molecule comprising combining a sample comprising an antibody with a monothiol reducing agent at a concentration in the range from 0.01 to 8 mM. Further provided is a method for the site-specific attachment of an effector molecule to an antibody comprising combining a sample comprising an antibody altered to contain cysteine 171, 156, 202 and/or 203 with a monothiol reducing agent at a concentration in the range of 0.01 to 8 mM. Preferably, the reaction is performed at a temperature in the range of 4° C. to 40° C., with 37° C. being preferred. Most preferably, the altered residue is residue 171.

Effector molecules can be attached to the antibodies of the invention directly or indirectly via engineered cysteine 171, 156, 202 and/or 203. It will be appreciated that where there are two or more effector molecules attached to the antibody these may be identical or different. It will also be appreciated that two or more effector molecules may be attached to the antibody at a single cysteine 171, 156, 202 or 203 site (preferably cysteine 171) by the use, for example, of a branched connecting structure to link two or more effector molecules and provide a single site of attachment.

Thus, effector molecules may be linked to a cysteine engineered antibody of the invention via a linker or scaffold which has a thiol-reactive group attached. One or two linker or scaffold molecules may be attached to the one or two of cysteine 156, 171, 202 or 203 residues engineered into the kappa light chains. The number of effector molecules attached, however, is not limited to one or two. The linker or scaffold molecule can be such that two, three, four or more effector molecules, as desired, can be attached. Examples of such linkers or scaffolds include those disclosed in GB application numbers 0518771.1 and 0600315.6. Alternatively, where the effector molecule is a protein or polypeptide the linkage may be achieved using recombinant DNA procedures, for example as described in European Patent Specification No. 392745.

It will be appreciated that effector molecules may be attached directly or indirectly via a spacer to the linker or scaffold molecule. For example, an effector molecule may be attached to a linker or scaffold molecule via a spacer that is cleavable using an enzyme or a spacer which is self-immoliative (see for example, U.S. Pat. No. 6,214,345).

The invention also provides a pharmaceutical composition comprising an altered antibody of the invention and a pharmaceutically acceptable diluent, excipient and/or carrier. Thus, a pharmaceutical composition may comprise an altered antibody of the invention which is conjugated to an effector molecule or molecules. Accordingly, provided is a pharmaceutical composition comprising an altered antibody of the class IgG comprising at least one human kappa light chain, or an epitope-binding fragment thereof comprising said alteration, wherein the alteration comprises replacing at least one residue selected from the group consisting of residues 171, 156, 202 and 203, numbered according to the Kabat numbering system, of the at least one kappa light chain with a cysteine residue and a pharmaceutically acceptable diluent, excipient and/or carrier. Most preferably, the altered residue is S171C.

Pharmaceutical compositions comprising an altered antibody of the invention find use in medicine, for example, in the treatment of diseases and disorders, such as inflammatory diseases, proliferative disorders and autoimmune disorders, e.g. rheumatoid arthritis, Crohn's disease, ulcerative colitis, carcinoma, lymphoma, leukaemia or lymphoid malignancies, ovarian cancer, breast cancer, colon cancer, bladder cancer, kidney cancer, liver cancer, lung cancer, pancreatic cancer, prostate cancer, SLE and multiple sclerosis. Thus, provided is the use of such a pharmaceutical composition in therapy.

The composition will usually be supplied as part of a sterile, pharmaceutical composition that will normally include a pharmaceutically acceptable carrier. This composition may be in any suitable form (depending upon the desired method of administering it to a patient).

Pharmaceutical compositions of the invention may be administered to a subject by any of the routes conventionally used for drug administration, for example they may be administered parenterally, orally, topically (including buccal, sublingual or transdermal, or using particle-mediated intracellular delivery directly into cells of the skin) or by inhalation. Particle-mediated delivery is described by Haynes, J R, 2004, Expert Opinion on Biological Therapy, 4:889-900. The most suitable route for administration in any given case will depend on the particular active agent, the disease or disorder involved, the subject, and the nature and severity of the disease and the physical condition of the subject. The pharmaceutical compositions may be administered in combination, e.g. simultaneously, sequentially or separately, with one or more other therapeutically active compounds.

The dosage to be administered of an altered antibody of the invention will vary according to the particular active agent, the cancer involved, the subject, and the nature and severity of the disease and the physical condition of the subject, the age, weight and gender of the subject, diet, time and frequency of administration, drug combination(s), reaction sensitivities, tolerance/response to therapy, and the selected route of administration; and that a physician will ultimately determine appropriate dosages to be used. This dosage may be repeated as often as appropriate. Generally, a therapeutically effective amount will be from 0.01 mg/kg to 100 mg/kg, preferably 0.1 mg/kg to 20 mg/kg. The frequency of dose will depend on the half-life of the altered antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months. If side effects develop the amount and/or frequency of the dosage can be altered or reduced, in accordance with normal clinical practice.

Pharmaceutical compositions may be conveniently presented in unit dose forms containing a predetermined amount of an active agent of the invention per dose. In particular, the dose at which the antibody molecule of the present invention is administered depends on the nature of the condition to be treated, the extent of the inflammation present and on whether the antibody molecule is being used prophylactically or to treat an existing condition.

For the treatment and/or prophylaxis of a disease or disorder in humans and animals pharmaceutical compositions comprising antibodies can be administered to patients (e.g., human subjects) at therapeutically or prophylactically effective dosages (e.g. dosages which result in tumour growth inhibition and/or tumour cell migration inhibition, or doses which improve or ameliorate the symptoms of the disease or disorder) using any suitable route of administration, such as injection and other routes of administration known in the art for antibody-based clinical products.

The compositions may contain from 0.1% by weight, preferably from 10-60%, or more, by weight, of the altered antibody of the invention, depending on the method of administration.

Compositions may be administered individually to a patient or may be administered in combination (e.g. simultaneously, sequentially or separately) with other agents, drugs or hormones.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

FIG. 1 shows the sequence of the heavy chain [panel (a); SEQ ID NO:1] and kappa light chain amino acid sequences of the human CTM01 antibody and CTM01(S171C) engineered antibody [panels (b) & (c); SEQ ID NOS:2 & 3, respectively]. The S171C mutation is underlined in bold typeface.

FIG. 2 shows the sequences of WT human cKappa constant region [(Kabat residues 108-214; panel (a); SEQ ID NO:4], and S156C, S202C and S203C mutants with the alteration in bold and underlined font [panels (b), (c) & (d); SEQ ID NOS:5, 6 & 7].

EXAMPLES

Figure 3:
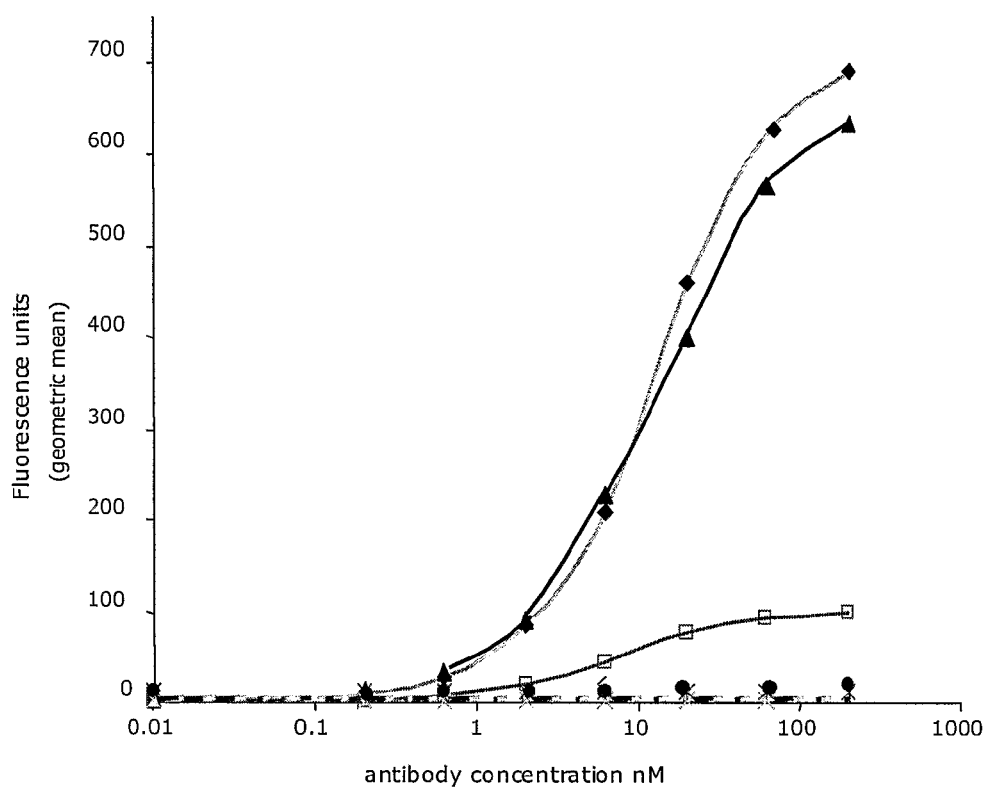
FIG. 3 shows the binding of dye labelled CTM01 S171C mutant IgG to cancer cells. ♦—DU145 S171C mutant cells; ▲—DU 145 wt; □—DU 145 wt/NHS ester; ×—LS174T S171C mutant; *—LS174T wt; ●—LS174T wt/NHS ester.

1. Mutagenesis of Serine 171 to Cysteine (S171C)

Site directed mutagenesis of serine 171, numbered according to the Kabat numbering system, of the kappa chain constant region of the engineered human antibody CTM01 was performed as follows: a vector encoding the CTM01 variable and constant region light chains in a human IgG4 framework was subjected to site-directed mutagenesis using a Stratagen Quikchange® site-directed mutagenesis kit (Cat. No. 200519-5, Stratagen, La Jolla, Calif.) using the forward primer, 5'-GCAGGACAGCAAGGACTGCACCTACAGC-CTCAG-3' (SEQ ID NO:4), and reverse primer, 5'-CTGAG-GCTGTAGGTGCAGTCCTTGCTGTCCTGC-3' (SEQ ID NO:5). The WT kappa chain sequence is shown in panel (b). The S171C mutation was verified by DNA sequencing and is shown in FIG. 1, panel (c). The heavy chain sequence is shown in FIG. 1 panel (a).

2. S156C S202C and S203C Cysteine Engineering

S156C, S202C and S203C altered antibodies were produced using a Stratagen Quikchange® site-directed mutagenesis kit (Cat. No. 200519-5, Stratagen, La Jolla, Calif.). Sequences are shown in FIG. 2, panels (b) to (d), along with the WT sequence in panel (a).

3. Expression of CTM01(S171C) in Hek 293 Cells

The heavy variable region of CTM01 was cloned into pVhGamma4p (as a HdIII-XhoI fragment; an internal XhoI site in the CTM01 heavy variable region was removed by site directed mutagenesis) and the kappa variable region was cloned into the expression vector, pVhCk(S171C), as a HdIII-BsiWI fragment. Separate DNA preparations were made for each construct and the antibody was transiently expressed by co-tranfection of the two constructs in Hek 293 cells grown in suspension in serum-free media.

4. Purification of CTM01(S171C)

IgG antibody present in culture supernatants following transient expression in Hek 293 cells was purified by protein A affinity chromatography. A protein A sepharose 4 fast flow column was prepared containing 20 ml of swollen gel and equilibrated with 200 ml 50 mM glycine/glycinate buffer, pH 8.8, eluting at 2 ml/min. Culture supernant (51) was loaded onto the column at 1.5 ml/min following adjustment of pH by addition of 125 ml of 2M Tris/HCl buffer, pH 8.5. The column was then washed with 550 ml 50 mM glycine/glycinate buffer, pH 8.8 at 3.35 ml/min until A280 nm readings returned to baseline. IgG was eluted with 100 ml of 0.1 M citrate buffer pH 3.0 and the fraction neutralized with 8 ml of 2M Tris/HCl, pH 8.5. Finally the material was buffer exchanged against 50 mM acetate, 2 mM EDTA buffer pH 5.5, concentrated to 45 ml and sterile filtered. For long term storage the IgG was further concentrated and buffer exchanged against 20% glycerol in 50 mM acetate, 2 mM EDTA buffer, pH 6.0.

5. Optimisation of CTM01(S171C) Thiol Reduction

Aliquots of S171C mutant IgG or wild type IgG (0.75 mg) in 0.1M acetate, 2 mM EDTA buffer, pH 6.0 were mixed with 2-mercaptoethylamine (2-ME) to give a range of final concentrations from 0 to 20 mM in a total of 1.5 ml. Reactions proceeded at 37° C. for 24 h and samples were buffer exchanged into phosphate buffered saline pH 7.5 containing 2 mM EDTA.

The degree of active thiol regeneration in the IgG was assessed by reaction with the fluorescent dye, AlexaFluor 488-C5-maleimide (Invitrogen Ltd). A 0.5 mM stock solution of the dye was prepared in DMF and a 200 μl aliquot added to each reduced IgG sample to a final volume of 1 ml and a molar excess of 15:1 dye:IgG. Reactions were allowed to proceed at 37° C. for 24 h and samples were buffer exchanged into phosphate buffered saline pH7.5 containing 2 mM EDTA. The degree of dye labelling of monomeric IgG was estimated following size exclusion hplc analysis where absorbance profiles at 280 nm and A494 nm were monitored. Area under the curve (AUC) values at both wavelengths allowed dye incorporation to be calculated as follows:

Dye per IgG=(AUC494 nm/54030)/(AUC280 nm−AUC494 nm×0.118)/208380.

Neglible amounts of dye were incorporated into either the mutant or wild type IgG in the absence of 2-ME reduction, indicating that the thiols on the mutant kappa cys171 were covalently blocked (Table 1). Conversely at high concentrations of 2-ME (20 mM) over 3 molecules of dye were incorporated per molecule wild type IgG, indicating that at least one cystine disulphide bond had been reduced. In the case of the mutant IgG, dye loading was higher at 4.8 dyes per IgG suggesting that at least one kappa cys171 had also been reduced. Surprisingly, it was found that at intermediate 2-ME concentrations, at between 1 and 2 mM, reduction was sufficient to result in the covalent linkage of just over 2 molecules of dye per IgG in the CTM01 S171C mutant IgG, whereas the reduction was not strong enough to result in disulphide bond disruption in the wild type IgG control, in so far as that on average, no more than one in two IgG molecules incorporated a single dye molecule.

TABLE 1

| AlexaFluor 488 labelling of S171C IgG | | |
|---|---|---|
| 2-ME | Dye molecules per IgG | |
| concentration (mM) | S171C mutant IgG | Wild type IgG |
| 0 | 0.08 | 0.05 |
| 1 | 2.2 | 0.5 |
| 1.5 | 2.7 | 0.5 |
| 2 | 2.8 | 0.5 |
| 3 | 3.2 | 0.56 |
| 4 | 3.4 | 0.7 |
| 10 | 3.6 | 1.9 |
| 20 | 4.8 | 3.5 |

Since the CTM01 S171C IgG differs from the wild type CTM01 at only the two kappa 171 residues, it was concluded that coupling of dye following reduction with 2-ME in the range 1 to 2 mM, gave close to the theoretical 2 dyes per IgG incorporation via the kappa cys171 thiols.

6. Testing Binding Potency and Specificity of AlexaFluor488-C5-Maleimide CTM01 S171C IgG Labelled Via the Kappa 171 Cysteine Residues The CTM01 antibody was raised against a human milk fat globule antigen (Aboud-Pirak et al, 1988, Cancer Research, 48:3188.) and recognizes a repeat epiptope on the muc-1 VNTR (Pietersz et al, 1997, Cancer Immunology and Immunotherapy, 44: 323-328). Binding of dye labelled CTM01 S171C IgG to muc-1 positive human cancer cell line, DU145 was compared to its binding to a muc-1 negative cancer cell line, LS174T by flow cytometry.

The S171C mutant IgG was labelled as above using prior reduction with 1.5 mM 2-ME, followed by incubation with a 15-fold molar excess of AlexaFluor 488-C5-maleimide to give a dye loading of 2.1 dyes per IgG. As a control, wild type IgG was treated under identical conditions to give a dye incorporation of 0.7 dyes per IgG. As a further control wild type CTM01 IgG was labelled via lysine modification, using the dye AlexaFluor488-NHS ester, to achieve a matched loading of 2 dyes per IgG.

The respective dye labelled antibodies were incubated 1 h on ice with single cell suspensions of either DU145 or LS174T cells at final concentrations of $0.8 \times 10^6$ cells per ml and IgG ranging from 0.2 to 200 nM. The assay buffer contained 10 mM sodium azide, 0.2% BSA, 2 mM EDTA in Dulbecco's phosphate buffered saline. The cells were washed with 4 ml chilled PBS, centrifuged at 2.5 g for 5min and the pellets re-suspended in 300 μl PBS.

Flow cytometry was performed using a FACScalibur instrument (Becton Dickenson). Fluorescence intensities were collected from the FL1 channel and plotted as geometric mean intensity versus IgG concentration (see FIG. 3).

The mutant hCTM01 with the label coupled via the kappa cys171 thiols showed a dose dependent increase in binding over 3 orders of magnitude to the muc-1 positive DU145 cells. The wild type hCTM01 labelled under identical conditions, but with 3-fold lower dye incorporation, resulted in at least a 6-fold lower degree of binding. Since in the latter case dye incorporation can only be acheived via disruption of the inter or intrachain disulphide of the IgG, it is likely that such disruption has a deleterious effect on antigen binding.

Dye labelling of antibodies is usually achieved via random covalent linkage to lysine side chains of the IgG. In the current example coupling of the NHS ester active dye via lysine residues of the wild type IgG has yielded a dye incorporation matched to that of kappa cys171-dye labelled S171C mutant IgG. In this situation equal binding potency is expected, however binding of the former is some 8% lower than that of the latter in the higher dose range, probably because of random labelling of lysine residues causing damage or hindrance to the antigen binding site. Conversely, labelling via the kappa cysteine 171 mutation, places the dye well away from the binding site thus does not interfere with antigen binding.

In each case binding specificity is confirmed by lack of binding to the antigen negative LS174T cell line.

7. Dye Labelling Via Reduced Cystine Disulphide Bonds Damages Antigen-binding Activity In a further experiment confirmation was sought on the deleterious effects of labelling via intra/inter chain reduced disulphides. Using conditions similar to the above IgG reduction and AlexaFluor488-C5-maleimide coupling reactions, it was found that reduction of hCTM01 S171C mutant with 5 mM 2-ME and reduction of wild type hCTM01 with 20 mM 2-ME resulted in similar incorporation of approximately 4 dyes per IgG.

Figure 4:
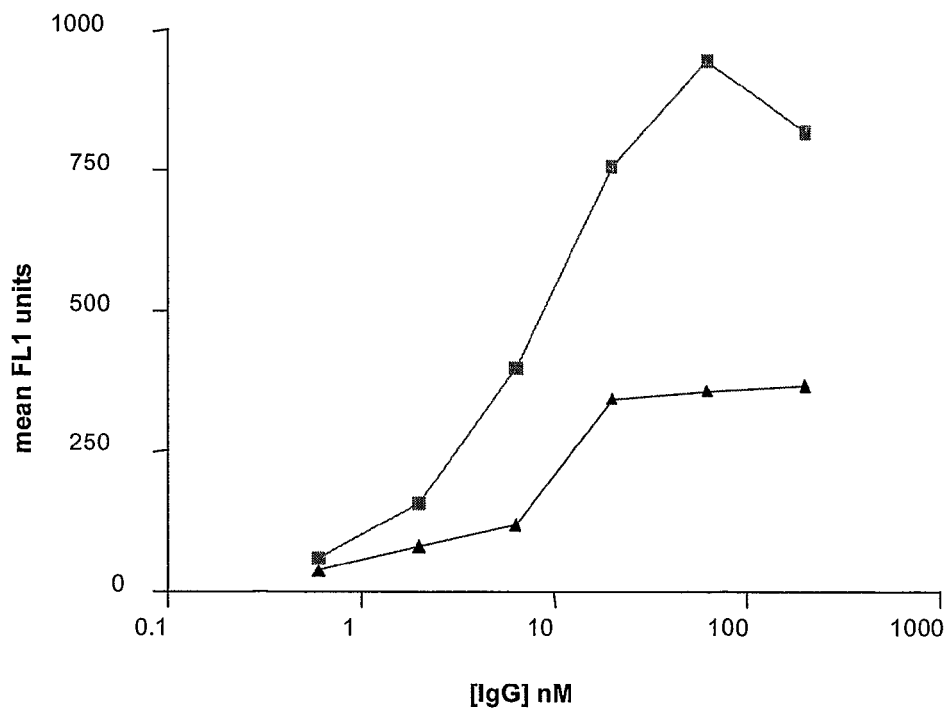
FIG. 4 shows the binding of AlexaFluor 488-labelled CTM01 IgG to T47D cells. ■—S171C mutant 3.9 dyes per IgG; ▲—wild type 3.6 dyes per IgG.

The binding potencies of these dye labelled antibodies were compared on muc-1 positive T74D human cancer cells by flow cytometry. Binding potency of the S171C mutant IgG showed a good dose dependent increase in binding over two orders of magnitude and only plateauing out above 100 nM concentration. In contrast the wild type IgG resulted in 2 to 3-fold lower binding with a binding plateau reached at only 20 nM IgG (see FIG. 4). Despite a similar drug incorporation on both IgGs, the wild type IgG displays a greater degree of damage to its antigen binding capacity. In this case at least two cystine disulphide bonds have been disrupted to account for the observed dye loading, whereas in the case of the mutant IgG, only one cystine disulphide disruption together with the kappa cysteine 171 residues can account for the observed dye loading.

In conclusion covalent linkage of maleimide adducts to IgGs via kappa cysteine 171 mutation, provides a much more satisfactory method of conjugate formation with respect to antigen binding activity than via reduced cystine thiols.

8. Conjugation of PEG[40 kD]-maleimide to CTM01 S171C IgG

Site specific conjugation of functional adducts to an IgG in a manner that does not affect antigen-binding potency is of potential benefit. Covalent linkage of PEG adducts of proteins and antibodies is a well known way of changing pharmacokinetics of the protein. It was therefore of interest to determine whether a high molecular weight PEG-maleimide species could be specifically coupled to the kappa cys171 thiols of CTM01 S171C IgG.

Aliquots of S171C mutant IgG or wild type IgG (1 mg) in 0.1M acetate, 2 mM EDTA buffer, pH 6.0 were mixed with 2-ME to a final concentration of 1.5 mM in 1.5 ml. After incubation at 37° C. for 24 h reaction mixtures were buffer exchanged into phosphate buffered saline pH 7.5 containing 2 mM EDTA. Aliquots of the reduced antibodies were treated with a 15-fold molar excess of PEG-maleimide (MW 40000), supplied by Shearwater polymers Inc. and allowed to react at 37° C. for up to 24 h. Reactions were examined over time and the extent of conjugation monitored by size exclusion hplc using Zorbax GF450 and Zorbax GF250 columns in series and a mobile phase comprising 10% ethanol in 0.2M sodium phosphate pH 7.0, eluting at 1 ml/min.

Peak areas under the A280 nm absorbance profiles were used to calculate the percentage product formation. Table 2 shows percentages of the IgG starting material running as an IgG monomeric peak with retention time of 19.3 min and those of the product peak of retention time 16.8 min i.e. of increased molecular size. After 1 h reaction time the CTM01 S171C IgG showed formation of 26.5% product whereas the wild type CTM01 control IgG only showed 6.6% product. By 18 h, the mutant IgG reaction showed that the majority of material had converted to product whereas for the control IgG reaction 88.8% remained as starting material.

The results clearly demonstrate that the majority of the high MW reaction product formed with the CTM01 S171C IgG must have arisen through specific covalent linkage of via the kappa chain cys171 thiols, since reaction of the control IgG, differing only at these residues, and treated in an identical manner, resulted in 5-fold less product.

TABLE 2

Formation of CTM01 S171C-PEG versus wild type-PEG IgG

| | S171C mutant IgG | | wild type IgG | |
|---|---|---|---|---|
| Reaction Time h | Peak Rt = 16.8' | Peak Rt = 19.3' | Peak Rt = 16.8' | Peak Rt = 19.3' |
| 1 | 26.5% | 73.5% | 6.6% | 93.4% |
| 18 | 52.5% | 47.5% | 11.2% | 88.8% |

We claim:

1. An altered antibody of the class IgG comprising at least one human kappa light chain with a variable region, and at least one human heavy chain with a variable region, or an epitope-binding fragment thereof comprising said alteration, wherein the alteration comprises replacing one of residues 171, 156, 202 and 203, numbered according to the Kabat numbering system, of the at least one kappa light chain with a cysteine residue.

2. The altered antibody according to claim 1, which is a Fab, a Fab' or a F(ab')$_2$.

3. The altered antibody according to claim 1, which is conjugated to one or more effector molecules.

4. The altered antibody according to claim 3, wherein the effector molecule comprises one or more cytotoxic agents, radionuclides or drug moieties, or one or more polymers.

5. The altered antibody according to claim 4, wherein the polymer is a PEG molecule.

6. The antibody molecule according to claim 5, wherein the PEG has a molecular weight in the range from about 20,000 to 40,000 Da.

7. The antibody molecule according to claim 5, wherein the PEG has a molecular weight of about 20,000 Da.

8. The altered antibody according to claim 4, wherein the drug moiety is a minor groove binder.

9. The altered antibody according claim 1, wherein the residue replaced by a cysteine is residue 171.

* * * * *

SEQUENCE LISTING

<160> NUMBER OF SEQ ID NOS: 7

<210> SEQ ID NO 1
<211> LENGTH: 447

```
<212> TYPE: PRT
<213> ORGANISM: Homo sapiens

<400> SEQUENCE: 1

Gln Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Met Arg Gln Ala Pro Gly Gln Gly Leu Glu Trp Ile
        35                  40                  45

Gly Trp Ile Asp Pro Gly Ser Gly Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Glu Lys Thr Thr Tyr Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 2
<211> LENGTH: 219
<212> TYPE: PRT
<213> ORGANISM: Homo sapiens

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ser Ser Lys Ser Leu Leu His Ser
            20                  25                  30

Asn Gly Asp Thr Phe Leu Tyr Trp Phe Gln Gln Lys Pro Gly Lys Ala
        35                  40                  45

Pro Lys Leu Leu Met Tyr Arg Met Ser Asn Leu Ala Ser Gly Val Pro
    50                  55                  60

Ser Arg Phe Ser Gly Ser Gly Ser Gly Thr Glu Phe Thr Leu Thr Ile
65              70                  75                  80

Ser Ser Leu Gln Pro Asp Phe Ala Thr Tyr Tyr Cys Met Gln His
            85                  90                  95

Leu Glu Tyr Pro Phe Thr Phe Gly Gln Gly Thr Lys Val Glu Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 219
<212> TYPE: PRT
<213> ORGANISM: Homo sapiens

<400> SEQUENCE: 3

Asp Ile Gln Met Thr Gln Ser Pro Ser Thr Leu Ser Ala Ser Val Gly
1               5                   10                  15

Asp Arg Val Thr Ile Thr Cys Arg Ser Ser Lys Ser Leu Leu His Ser
            20                  25                  30

Asn Gly Asp Thr Phe Leu Tyr Trp Phe Gln Gln Lys Pro Gly Lys Ala
        35                  40                  45

Pro Lys Leu Leu Met Tyr Arg Met Ser Asn Leu Ala Ser Gly Val Pro
    50                  55                  60

Ser Arg Phe Ser Gly Ser Gly Ser Gly Thr Glu Phe Thr Leu Thr Ile

```
                65                  70                  75                  80
Ser Ser Leu Gln Pro Asp Asp Phe Ala Thr Tyr Tyr Cys Met Gln His
                    85                  90                  95

Leu Glu Tyr Pro Phe Thr Phe Gly Gln Gly Thr Lys Val Glu Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Cys
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 107
<212> TYPE: PRT
<213> ORGANISM: Homo sapiens

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Cys Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

-continued

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Cys Ser
                85                  90                  95

Pro Val Thr Lys Ser Phe Asn Arg Gly Glu Cys
            100                 105

<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Cys
                85                  90                  95

Pro Val Thr Lys Ser Phe Asn Arg Gly Glu Cys
            100                 105